(12) United States Patent
Cleary et al.

(10) Patent No.: US 6,234,791 B1
(45) Date of Patent: May 22, 2001

(54) ORTHODONTIC COUPLING PIN

(75) Inventors: James D. Cleary, Glendora; Russell A. Jordan, Rancho Cucamonga, both of CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/197,309

(22) Filed: Nov. 20, 1998

(51) Int. Cl.[7] ................................................. A61C 3/00
(52) U.S. Cl. ................................................. 433/18; 433/19
(58) Field of Search .......................... 433/18, 19, 21, 433/14

(56) References Cited

U.S. PATENT DOCUMENTS

| | | | |
|---|---|---|---|
| 3,508,332 | * 4/1970 | Armstrong | 433/21 |
| 3,793,730 | * 2/1974 | Begg et al. | 433/14 |
| 3,798,773 | 3/1974 | Northcutt | 433/19 |
| 4,462,800 | 7/1984 | Jones | 433/19 |
| 4,551,095 | 11/1985 | Mason | 433/19 |
| 4,708,646 | 11/1987 | Jasper | 433/19 |
| 4,826,372 | 5/1989 | Kendall | 411/43 |
| 5,017,133 | 5/1991 | Miura | 433/20 |
| 5,352,116 | 10/1994 | West | 433/19 |
| 5,435,721 | 7/1995 | Vogt | 433/19 |
| 5,651,672 | 7/1997 | Cleary et al. | 433/19 |
| 5,711,667 | 1/1998 | Vogt | 433/19 |
| 5,718,576 | 2/1998 | Schnaitter et al. | 433/22 |

OTHER PUBLICATIONS

1996–1997 Orthodontic Product Catalog, 3M Unitek, pp. 1–46, 1–50, 1–51.

* cited by examiner

*Primary Examiner*—John J. Wilson
(74) *Attorney, Agent, or Firm*—James D. Christoff

(57) ABSTRACT

An orthodontic pin has a high strength intermediate section that resists bending in use, as well as a softer, more compliant outer end section. The softer outer end section can be readily bent in an arc for attachment to an orthodontic appliance or device. The coupling pin of the invention may be used to couple one orthodontic appliance or device to another, or alternatively may be part of an orthodontic device that is ultimately coupled to another device or appliance.

16 Claims, 4 Drawing Sheets

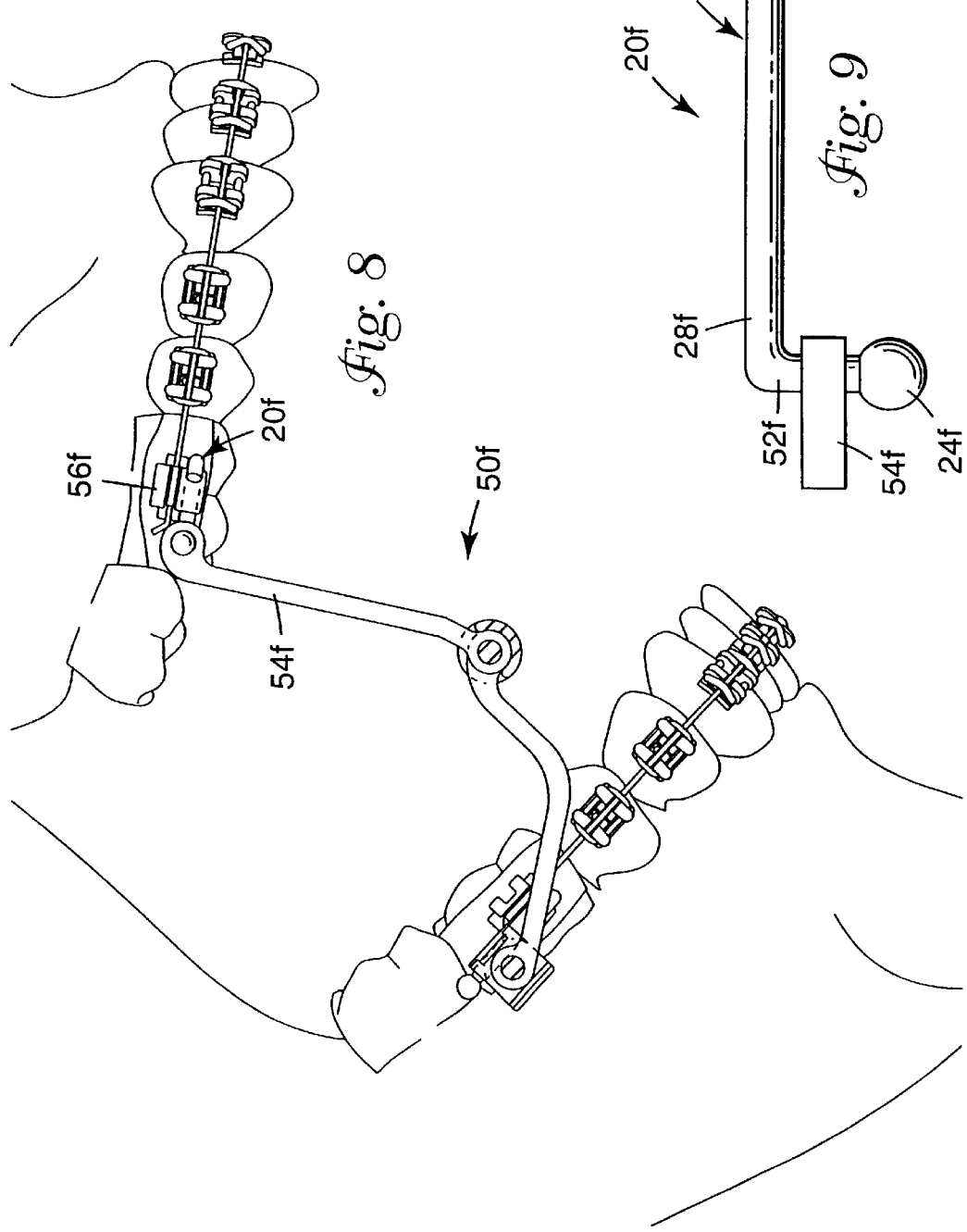

ORTHODONTIC COUPLING PIN

BACKGROUND OF THE INVENTION

1. Field of the Invention

This invention relates to a coupling used in orthodontic treatment to connect orthodontic appliances or devices together.

2. Description of the Related Art

Orthodontic therapy is a specialized form of treatment within the field of dentistry. Orthodontic treatment involves movement of malpositioned teeth to orthodontically correct locations. Orthodontic treatment often greatly improves the aesthetic appearance of the patient's teeth and also improves the patient's occlusion, so that when the jaws are closed the upper teeth are in proper positions relative to the lower teeth.

Orthodontic treatment is often carried out by a system of tiny appliances, wires and other components that are commonly known collectively as "braces". Typically, a small appliance known as a bracket is connected to each of the patient's anterior, cuspid and bicuspid teeth and an archwire is placed in a slot of each bracket. The archwire forms a track to guide movement of the brackets and the associated teeth to desired positions. Typically, end sections of the archwires are held by appliances known as buccal tubes that are secured to the patient's molar teeth.

In some instances, it is necessary or desirable to use coupling pins during the course of orthodontic treatment. Many of the earliest orthodontic pins were used to couple archwires to brackets, including certain types of orthodontic brackets that were known as "Begg" brackets. Begg brackets have an upright tube with a passage for receiving the pin, and the pin has a head that captures the archwire between the tube and the associated tooth.

Other known types of brackets are made with an auxiliary passage that can be used for receiving a pin for connection to components other than archwires. For example, brackets known as "vertical slot" brackets have a passage that is located lingually (i.e., in a direction toward the patient's tongue) of a slot that receives the archwire. Typically, the passage extends in a generally occlusal-gingival direction (i.e., in a direction along a reference axis extending from the outer tips of the teeth to the gingiva or gums), which may or may not represent a true vertical direction. Vertical slot brackets enable the orthodontist to install a pin in selected brackets as desired, and then subsequently use the pin to couple those brackets to other devices or appliances.

Buccal tubes also often have auxiliary passages that can be used if desired for receiving a coupling pin. Typically, such auxiliary passages extend in side-by-side relation to the passage that receives the end section of the archwire. Buccal tubes are especially useful as connection locations for orthodontic pins, because the relatively large roots of the molar teeth associated with the buccal tubes provide a strong anchor for moving other teeth during the course of treatment.

Orthodontic coupling pins have enlarged heads that serve to couple a device, appliance or other component to the pin and also serve to prevent the pin from moving in one direction through the passage of the associated bracket or buccal tube. Often, the head of the pin has a somewhat spherical or ball shape. Alternatively, however, the head of the pin may be somewhat "L"-shaped or "T"-shaped. In some instances, coupling pins are known as "hooks", particularly if the pin has an "L"-shaped head or a "T"-shaped head. Coupling pins used to connect archwires to brackets (such as Begg brackets) are often known as lock pins.

Orthodontic pins that are received in auxiliary passages of brackets or buccal tubes are sometimes connected to devices known as force modules that provide a compressive force, a tensile force or both. In some instances, force modules are used in intra-arch applications where one tooth or a selected set of teeth are moved relative to other teeth of the same jaw. In other instances, force modules are used in inter-arch applications where one tooth, a selected set of teeth or an entire dental arch is moved relative to the opposite dental arch.

An example of use of a force module in an intra-arch application is closure of a relatively large space between adjacent teeth as might occur, for example, if a tooth has been extracted or is otherwise missing. To close the space between adjacent teeth, the practitioner may elect to place a pin in the auxiliary vertical slot of each bracket adjacent the space, and then connect an elastomeric force module between the pins. The elastomeric force module exerts a tensile force on the pins and consequently on the associated brackets in order to move the teeth toward each other over a period of time to close the space.

A variety of orthodontic force modules used in tension for such space closure applications are known. Examples include ring-shaped modules (such as intraoral elastics from 3M Unitek Corporation) and dogbone-shaped modules having outer, ring-shaped ends with straight shank middle sections (such as "K" modules from 3M Unitek Corporation). Other examples include chain type force modules which comprise a series of interconnected rings (such as "C" modules from 3M Unitek Corporation).

The orthodontic treatment of many patients includes correction of the alignment of the upper dental arch with the lower dental arch. For example, certain patients have a condition referred to as a Class II malocclusion wherein the lower dental arch is located an excessive distance rearwardly of the upper dental arch when the jaws are closed. Other patients have an opposite condition referred to as a Class III malocclusion wherein the lower dental arch is located forwardly of the upper dental arch when the jaws are closed.

Orthodontic treatment of Class II and Class III malocclusions are commonly corrected by movement of the upper dental arch as a single unit relative to movement of the lower dental arch as a single unit. To this end, pressure is often applied to each dental arch as a unit by applying pressure to attachments that are connected to the patient's brackets or archwires. In this manner, the Class II or Class III malocclusion can be corrected at the same time that the archwires and brackets are used to move individual teeth to desired positions.

A variety of devices are used for treatment of Class II and Class III malocclusions. Examples include flexible members as described in U.S. Pat. Nos. 4,708,646 and 5,352,116. Another type of member useful in such applications is described in U.S. Pat. No. 5,651,672. U.S. Pat. Nos. 3,798,773, 4,462,800 and 4,551,095 disclose telescoping tube assemblies that urge the jaws toward positions of improved alignment.

Typically, orthodontic coupling pins are connected to brackets, buccal tubes or other appliances by threading the shank of the pin through the auxiliary passage until an outer end section of the pin projects past the passage. Next, the practitioner uses a pair of pliers or other tool having small tips to grasp the outer end section and bend the outer end section in an arc, such as a 90 degree arc. The pin can be removed when desired by straightening the outer end section into a position of coaxial alignment with remaining sections of the shank. Pins may also be connected to appliances by use of a deformable stop member that is clinched onto the outer end section of the pin once the pin is in place.

U.S. Pat. No. 5,718,576 describes an improved orthodontic coupling pin that is especially useful during treatment of Class II malocclusions. The pin of certain embodiments set out in U.S. Pat. No. 5,718,576 has an offset shank section that reduces stresses on the pin in use and consequently reduces the likelihood of breakage of the pin or other associated devices or appliances. Optionally, the outer end section of the shank has a reduced cross- sectional area that is smaller than cross-section al area than remaining areas of the shank, so that the end section can be readily bent by the orthodontist as needed after insertion of the shank into an appliance.

Additionally, some orthodontic devices include a coupling that comprises a pin or pin shank adapted to be received in an auxiliary passage of a bracket, buccal tube or other appliance. For example, pending U.S. patent application Ser. No. 09/06,746 entitled "MANDIBULAR REPOSITIONING DEVICE" describes an orthodontic device that includes a pivotal connector having a shank. Like the pins with the enlarged heads mentioned above, the shank of the connector described in pending U.S. Ser. No. 09/063,746 has an outer end section that is adapted to be bent in an arc in order to securely couple the device to a buccal tube or other appliance once the shank has been inserted into the auxiliary passage.

SUMMARY OF THE INVENTION

The present invention is directed to an orthodontic coupling pin for use with an orthodontic appliance such as a bracket, buccal tube or the like. The pin has an elongated shank and an enlarged head connected to the shank. The shank has an outer end section remote from the head and an intermediate section between the outer end section and the head. The intermediate section is made of a material having a certain yield stress, and the outer end section is made of a material having a yield stress that is less than the yield stress of the material of the intermediate section.

The present invention is an advantage, since the relatively low yield stress of the material of the outer end section of the coupling pin enables the outer end section to be readily bent in an arc as needed during connection of the pin to an appliance. Additionally, the relatively high yield stress of the material of the intermediate section of the shank provides a high strength construction that resists unwanted bending or fracture during use. The relatively high yield stress of the material of the intermediate section is an advantage because the coupling pin may be subject to substantial forces while in use in the oral cavity, such as might occur during chewing when the jaws are opened and closed.

These and other aspects of the invention are described in more detail in the text that follows and are illustrated in the accompanying drawings.

BRIEF DESCRIPTION OF THE DRAWINGS

FIG. 8 is a partially schematic side elevational view of a patient with a mandibular repositioning device having a coupling pin according to the present invention;

FIG. 9 is an enlarged, fragmentary plan view of the device shown in FIG. 8 showing the coupling pin as it appears before being bent during installation.

DETAILED DESCRIPTION OF THE PREFERRED EMBODIMENTS

Figure 1:
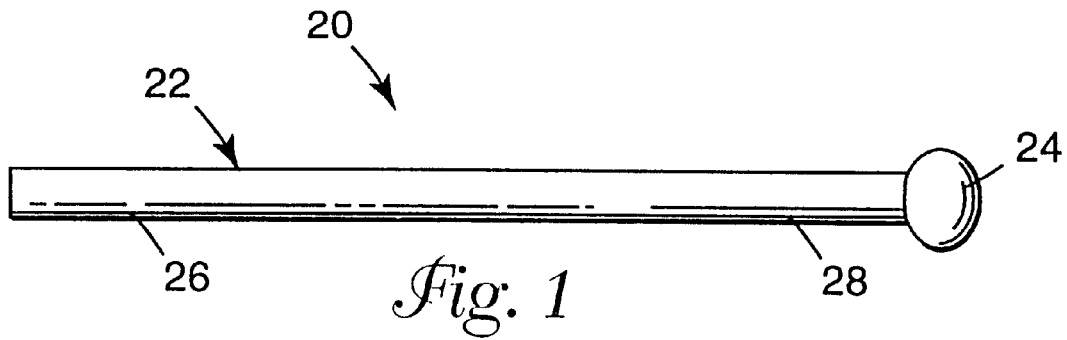
FIG. 1 is an enlarged side elevational view of an orthodontic coupling pin constructed in accordance with one embodiment of the present invention.

An orthodontic coupling pin according to one embodiment of the invention is illustrated in FIG. 1 and is broadly designated by the numeral 20. The pin 20 includes an elongated, initially straight shank 22 that preferably has a circular configuration in cross-sectional view. An enlarged head 24 is connected to the shank 22, and in this embodiment has a somewhat ball or spherical configuration.

The shank 22 includes an outer end section 26 that is remote from the head 24. The shank 22 also includes an intermediate section 28 that is located between the outer end section 26 and the head 24. In the illustrated embodiment, the intermediate section 28 is directly connected to the head 24 although other constructions are also possible. For example, a third section could be located between the intermediate section 28 and the head 24.

The intermediate section 28 is made of a material having a certain yield stress. The outer end section 26 is also made of a material having a certain yield stress. The yield stress of the material of the outer end section 26 is less than the yield stress of the material of the intermediate section 28.

As a consequence, the outer end section 26 is relatively easy to bend into a configuration adapted to retain the pin 20 in a passage of an orthodontic appliance. For example, the outer end section 26 may be bent to a generally "L"-shaped configuration or a generally "U"-shaped configuration. Such bending substantially prevents the pin 20 from unintentional detachment from the appliance during the course of treatment.

The relatively high yield stress of the material of the intermediate section 28 provides a stiff, high strength portion that is resistant to deformation. As a consequence, the practitioner can be assured that the configuration of the intermediate section 28 will not change in ordinary use. For example, in certain applications it may be highly important for the head 24 to remain in a certain position relative to the accompanying appliance during the course of treatment, and in that instance the relatively high yield stress of the material of the intermediate section ensures that the intermediate section will not bend and that the head 24 will not move laterally or in other directions relative to the appliance.

Preferably, the outer end section 26 is fully or at least partially annealed, and is preferably annealed to a greater extent than the material of the intermediate section 28. The difference in the amount of annealing between the outer end section 26 and the intermediate section 28 enables the yield stress of the outer end section 26 to be less than the yield stress of the intermediate section 28. The relatively low yield stress of the outer end section 26 enables the latter to be more compliant or softer than the intermediate section 28, and enables the outer end section 26 to be permanently deformed with less effort than the effort required to permanently deform the intermediate section 28.

The pin 20 may be made by a casting, machining, cold-heading or metal injection molding process. Preferably, the head 24 is integrally connected to the shank 22 and the pin 20 is made of a non-corrosive, non-toxic material such as 300 series stainless steel.

Conventional pins are made, for example, of a stainless steel material (such as type 303) that is annealed to allow easy machining and forming of the ball head. By contrast, and in accordance with the present invention, the entire pin 20 is initially made by a cold drawing and cold heading process using, for example, type 302 or 304 stainless steel. Such a process enables the intermediate section 28 to have a relatively high yield stress due to the retained cold work. Subsequently, the outer end section 26 is annealed or partially annealed, and as a result can be more easily deformed past its yield point than the intermediate section 28.

Figure 2:
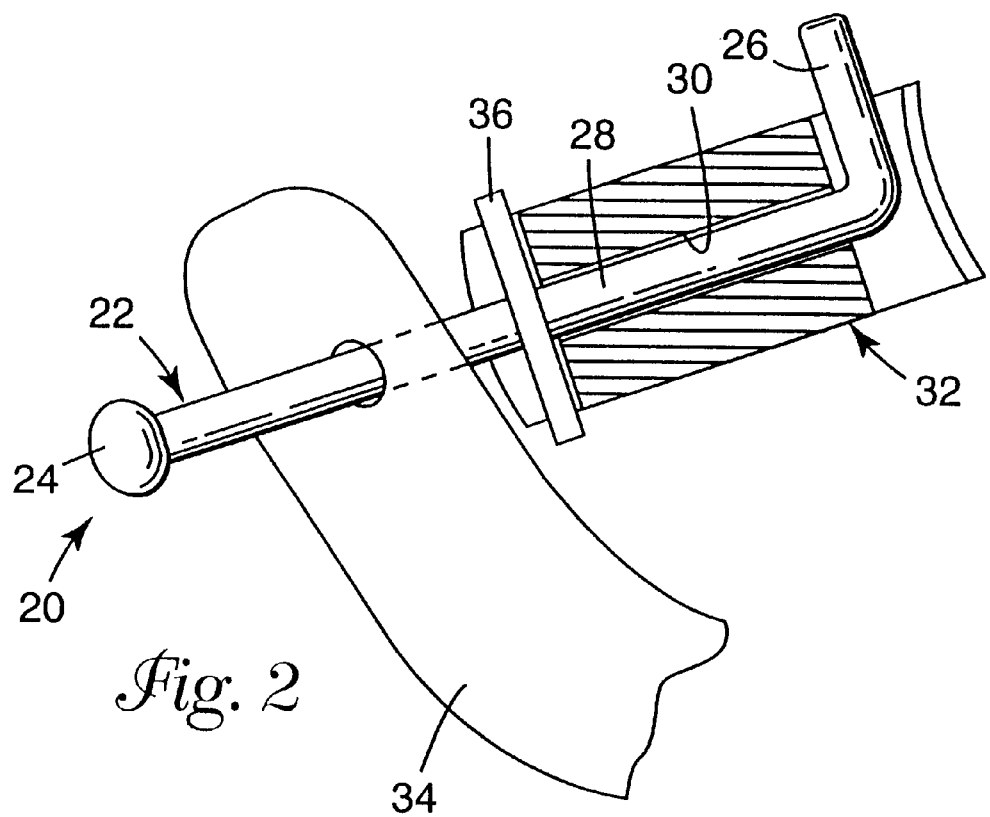
FIG. 2 is an enlarged side elevational view in partial section of the orthodontic coupling pin depicted in FIG. 1 along with a force module and a buccal tube for exemplary purposes, showing the pin as it appears after installation, and additionally showing an optional annular stop connected to the pin to limit movement of the pin in the buccal tube.

In FIG. 2, the pin 20 is shown for exemplary purposes as it might appear in one application of use. In FIG. 2, the intermediate section 28 is received in an auxiliary passage 30 of a buccal tube appliance 32 (shown in partial section and not in full detail). The outer end section 26 has been bent by the practitioner in an arc to form a generally "L"-shaped tip that prevents disengagement of the pin 20 from the buccal tube 32.

The pin 20 in the example of FIG. 2 is used to connect a resilient force device or force module 34 to the buccal tube appliance 32. As shown, the force module 34 has an opening that receives the shank 22. As an example, the force module 34 may be of the type described in U.S. Pat. Nos. 5,453,721 or 5,651,672. Alternatively, the force module 34 may be replaced with other types of force modules or other devices as desired.

The pin 20 as shown in FIG. 2 has been provided with an optional annular stop 36 that is fixed to the shank 22 between the head 24 and the outer end section 26. The stop 36 abuts one side of the buccal tube appliance 32, and consequently prevents further movement of the head 24 in a direction toward the buccal tube appliance 32. The force module 34 is freely slidable along the shank 22 in the space between the head 24 and the stop 36.

The stop 36 as explained above is optional and may be welded or brazed to the shank 22. Alternatively, the stop 36 may be made of a deformable material having a split-cylindrical sleeve-like configuration that is initially open to receive the shank 22 and then clenched to a closed position in order to crimp the stop 36 to the shank 22. Other constructions are also possible.

As used herein, the phrase "enlarged head" means any type of structure or configuration that projects outwardly from the shank 22 in directions perpendicular to the longitudinal axis of the shank 22. Consequently, the head 24 may have a configuration other than the somewhat spherical shape as shown in FIGS. 1 and 2.

Figure 3:
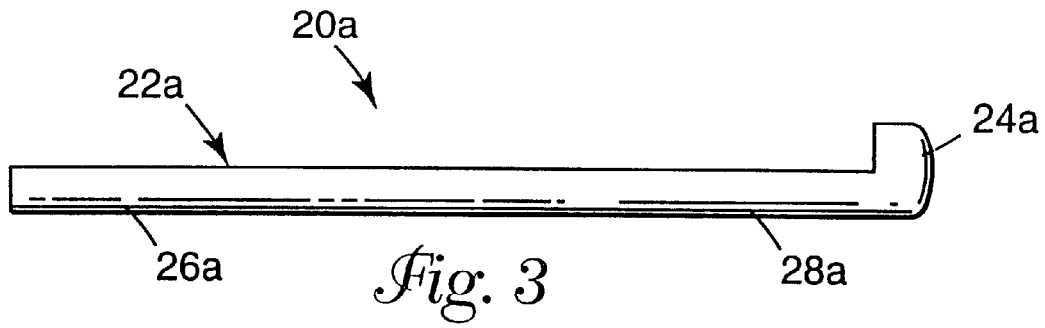
FIG. 3 is an enlarged side elevational view of an orthodontic coupling pin constructed in accordance with another embodiment of the invention.
Figure 4:
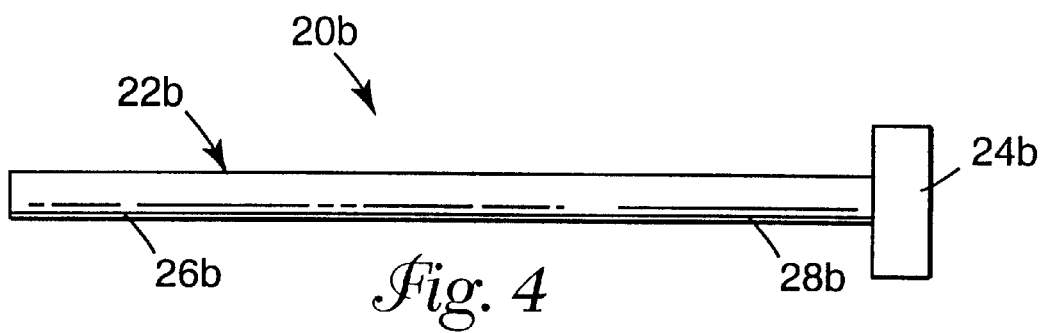
FIG. 4 is a view somewhat similar to FIGS. 1 and 3 except in accordance with another embodiment of the invention.

For example, the pin 20a illustrated in FIG. 3 has a somewhat "L"-shaped head 24a that projects sufficiently past a shank 22a in a lateral direction to prevent movement through the passage of the associated appliance. The shank 22a and the head 24a may have a circular or rectangular configuration in longitudinal view. Optionally, both the shank 22a and the head 24a have a generally flat configuration with approximately the same thickness.

The pin 20a also has an outer end section 26a and an intermediate section 28a that are identical to the outer end section 26 and the intermediate section 28 respectively described above. Other elements and aspects of the pin 20a are also identical to the corresponding aspects of the pin 20. Accordingly, a detailed description of such sections and other elements and aspects need not be repeated.

An orthodontic coupling pin 20b according to another embodiment of the invention is somewhat similar to the pin 20 and pin 20a described above, but in this instance the pin 20b has a head 24b with a somewhat "T"-shaped configuration. The overall width of the head 24b is greater than the width of the shank 22b, and is wider than the auxiliary passage of the associated appliance. Optionally, both the shank 22b and the head have a generally flat configuration with the same thickness, although other cross-sectional shapes are also possible. As can be appreciated, the heads 24a, 24b may also be called "hooks", and serve to couple an orthodontic appliance or device to the pin 20b and hence to the appliance or device to which the pin 20b is coupled.

The pin 20b has an outer end section 26b and an intermediate section 28b that are identical to the outer end section 26 and the intermediate section 28 respectively described above. Other elements and aspects of the pin 20b are preferably identical to the corresponding aspects of the pin 20 described above. As such, a detailed description of such sections, aspects and elements will not be repeated.

Figure 5:
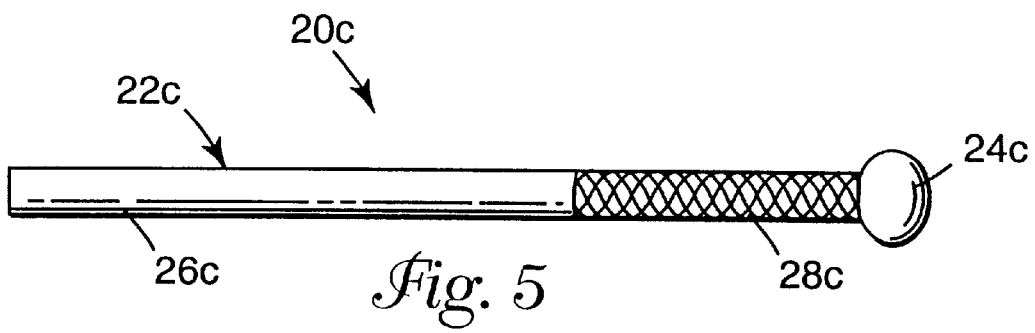
FIG. 5 is an enlarged side elevational view of an orthodontic coupling pin according to yet another embodiment of the invention.

An orthodontic pin 20c constructed in accordance with another embodiment of the invention is shown in FIG. 5. The pin 20c has a shank 22c that in this instance is made of a number of lengths of wire strands. For example, the shank 22c may be a multi-strand wire section having a number of relatively small diameter strands that are twisted, coaxial and/or braided together.

The shank 22c has an outer end section 26c and an intermediate section 28c. A head 24c is connected to the intermediate section 28c. Optionally, the head 24c is a solid ball-shaped structure that is brazed, soldered (by, e.g., silver solder) or welded to the multi-stranded intermediate section 28c. Heads with other configurations and heads that are integrally connected to the intermediate section 28c are also possible.

The outer end section 26c is tinned with a braze material or solder material (such as silver solder) to provide a solid cross-sectional construction. However, the braze or solder material is omitted from the intermediate section 28c. As a consequence, the intermediate section 28c is relatively flexible due to the stranded construction that remains, while the now-solid outer end section 26c is relatively stiff. The outer end section 26c has a yield stress that is less than the yield stress of the intermediate section 28c.

The relatively flexible intermediate section 28c is an advantage in certain instances where a yielding movement is desired. For example, if the pin 20c is used to couple an inter-arch force module to a buccal tube, the intermediate section 28c may move laterally when the patient's jaws are opened to a relatively large extent. The flexible intermediate section 28c may serve to reduce breakage of the force module, the buccal tube or other appliances in such instances.

Figure 6:
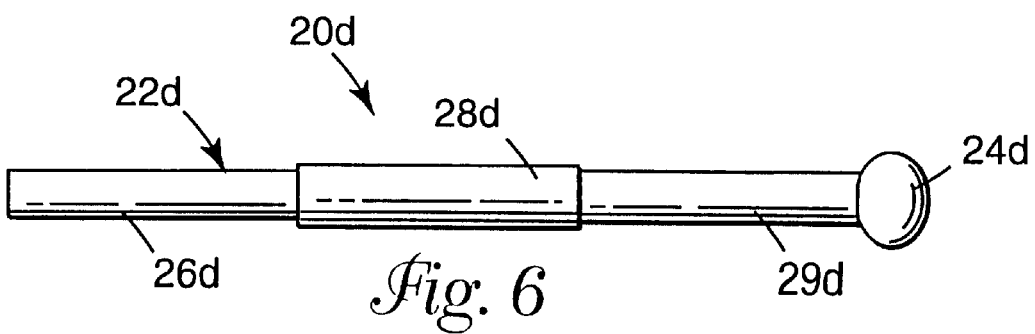
FIG. 6 is a view somewhat similar to FIG. 5 but in accordance with still another embodiment of the invention.

An orthodontic coupling pin 20d according to another embodiment of the invention is illustrated in FIG. 6, and comprises a shank 22d with a head 24d, an outer end section 26d and an intermediate section 28d. In addition, the shank 22d includes a third section 29d that is located between the intermediate section 28d and the head 24d.

In the embodiment shown in FIG. 6, the outer end section 26d is constructed of a length of solid material. The intermediate section 28d has an outer, cylindrical connector that surrounds a portion of solid material extending from the outer end section 26d. The cylindrical connector also surrounds a portion of material extending from the third section 29d and consequently functions as a sleeve coupler to couple the sections 26d, 29d together. As an option not shown in the drawings, the portions received within the intermediate section 28d have a smaller diameter than the diameter of the sections 26d, 29d, so that the outer diameter of the intermediate section 28d is essentially the same as the outer diameter of the sections 26d, 29d.

The outer end section 26d has a yield stress that is less than the yield stress of the intermediate section 28d. Preferably, the third section 29d is made of a relatively flexible material such as the multi-strand material of the intermediate section 28c described above, so that the third section 29d has a stiffness that is less than the stiffness of the intermediate section 28d.

As another alternative, the sections 26d, 28d are made of a unitary body and the section 28d has a recess or socket to receive a portion of material extending from the third section 29d. The material extending from the third section 29d is brazed, soldered, welded or glued to the section 28d within the recess or socket.

In the various embodiments set out above, the coupling pins of the invention have been described as independent or initially separate components that are used to couple orthodontic appliances or devices together. However, the coupling pin of the present invention can also be incorporated as part of an orthodontic appliance or device for facilitating connection to another appliance or device. An example of such a concept is found in FIG. 7, where an orthodontic uprighting spring 40e has a shank 22e and presents a coupling pin 20e.

In more detail, the shank 22e includes an outer end section 26e and an intermediate section 28e. The outer end section 26e is made of a material having a yield stress that is less than the yield stress of the material of the intermediate section 28e. Consequently, the intermediate section 28e is relatively stiff and resists bending, while the outer end section 26e may be readily bent in an arc as desired in order to secure the uprighting spring 40e to an appliance such as a bracket having an auxiliary vertical slot.

Figure 7:
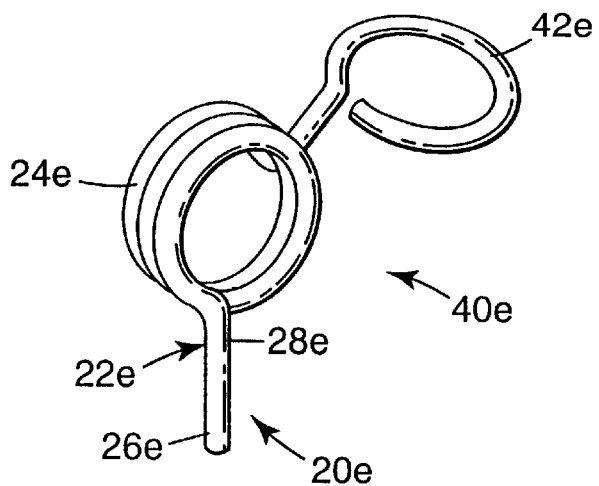
FIG. 7 is an enlarged perspective view of an orthodontic uprighting spring that includes a coupling pin according to the present invention.

In the embodiment shown in FIG. 7, the uprighting spring 40e includes an enlarged head 24e that is connected to the shank 22e next to the intermediate section 28e. The head 24e in this instance comprises a loop that functions as a coil spring. An outer end section 26e of the shank 22e is adapted to be inserted into an appliance such as the passage of a vertical slot bracket. An end section of the shank 22e remote from the outer end section 26e comprises a connector loop 42e that may be coupled, for example, to an archwire in order to provide an uprighting force on a tooth bonded to the appliance.

Optionally, other types of heads may be provided. For example, the head may be an initially separate component that is fixed by welding, brazing, clenching or the like to a section of wire that has been formed into the uprighting spring 40e. Other constructions are also possible. The outer end section 26e is made of a material having a yield stress that is less than the yield stress of the material of the intermediate section 28f.

A mandibular repositioning device 50f is illustrated in FIGS. 8 and 9, and includes a coupling pin 20f of the type described in other embodiments above. That is, the coupling pin 20f includes a shank 22f with an outer end section 26f and an intermediate section 28f. The outer end section 26f is made of a material having a yield stress that is less than the yield stress of the intermediate section 28f, such that the outer end section 26f is more compliant than the intermediate section 28f.

The intermediate section 28f in this instance includes an L-shaped portion 52f that extends through a hole or opening of a distal end portion of a link 54f. An enlarged head 24f is connected to the intermediate section 28f and is larger than the hole. The head 24f prevents the shank 22f from detaching from the link 54f. In other aspects, the mandibular repositioning device 50f is similar to the device described in applicant's pending U.S. application Ser. No. 09/063,746 mentioned above, which is incorporated herein by reference.

The outer end section 26f is adapted to be inserted through an auxiliary passage of a buccal tube appliance 56f and its relatively low yield stress enables the practitioner to easily bend the outer end section 26f in an arc to secure the coupling pin 20f to the buccal tube appliance 56f when desired. FIG. 9 shows the shank 22f as it initially appears in its straight configuration before it is bent.

Figure 10:
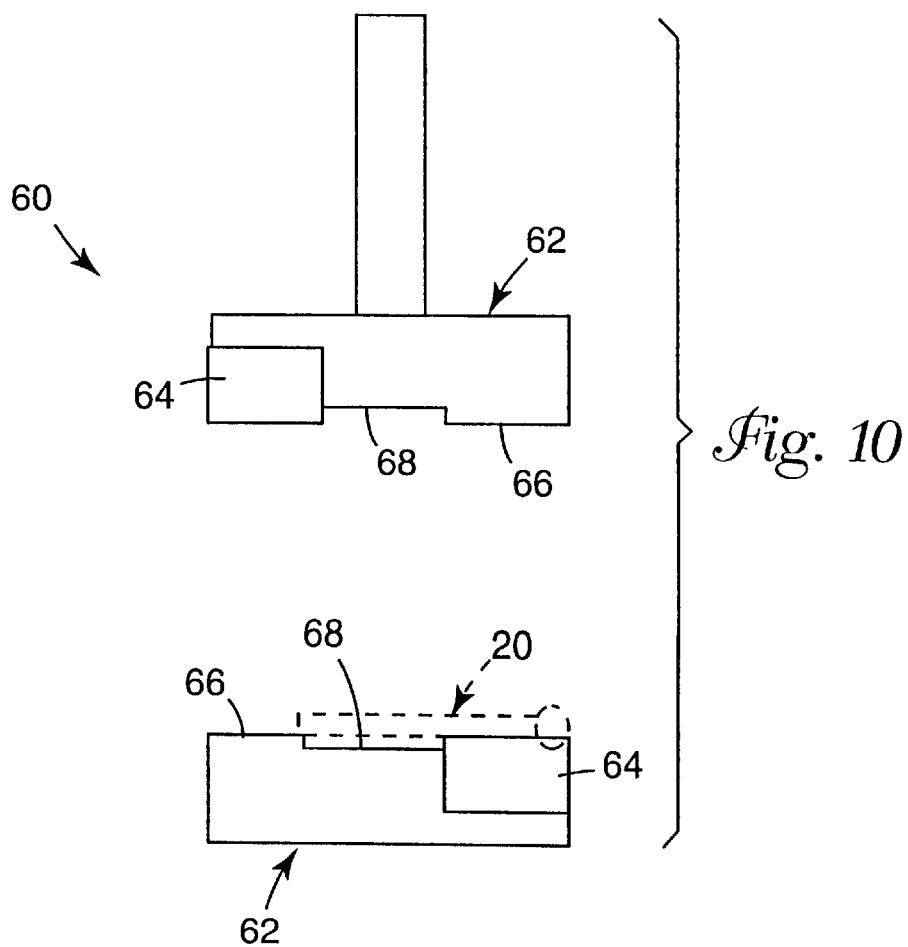
FIG. 10 is a reduced schematic illustration of an example of a jig useful in manufacturing the coupling pins of the present invention.

FIG. 10 is an example of an apparatus 60 useful for making a coupling pin of the present invention. In particular, the apparatus 60 is useful for providing additional annealing on an outer end section of the coupling pin. The apparatus 60 includes two electrodes 62, 62, each of which is connected to one output terminal of a resistance welder.

Each of the electrodes 62, 62 has a channel that receives an electrically non-conductive insert 64. The insert may be made of, for example, Bakelite brand synthetic resin materials or polycrystalline ceramic. As shown in FIG. 10, the insert 64 of the upper electrode 62 is oppositely oriented relative to the insert 64 of the lower electrode 62.

Each electrode 62 includes a support 66 remote from the insert 64. Additionally, a recess 68 extends between the support 66 and the insert 64 of each electrode 62. Each support 66 and each insert 64 is also provided with an appropriately-configured cavity that is adapted to complementally receive and support portions of a coupling pin of the present invention, such as coupling pin 20.

In FIG. 10, the pin 20 is shown is dashed lines to indicate its orientation in the apparatus 60 when resting in the cavities of the lower electrode 62. Once the pin 20 is placed on the lower electrode 62 as shown, the upper electrode 62 is lowered to a position of secure contact with the pin 20. The recesses of the supports 66 and the inserts 64 prevent unintentional movement of the pin 20 during closure of the electrodes 62, 62 and also during the subsequent annealing process.

Next, the resistance welder is activated to provide current to the electrodes 62, 62. As current flows along the length of the pin 20 between the supports 66, 66, the portion of the pin 20 that lies in the recesses 68, 68 is heated and annealed. Remaining portions of the pin 20 are in direct electrical contact with the electrodes 62, 62 and consequently are not heated or annealed to the same extent as the portions lying in the recesses 68, 68. Optionally, the pin 20 is cooled immediately after the annealing process with dry cool air.

A number of variations on the particular embodiments described in detail above may be apparent to those skilled in the art. For example, various sections of the pin shanks described above may differ in overall dimensions or have configurations other than that shown, and a variety of other types of heads can also be employed. The pin shanks may also be offset or bent at angles as described in U.S. Pat. No. 5,718,576, and need not have a constant cross-sectional area or configuration along its length. Moreover, the coupling pin of the invention can be used as part of a variety of orthodontic devices or appliances other than that which are shown, and may be fixed or releasably coupled to those devices or appliances. The coupling pin can also be connected to linkage that, in turn, is connected to orthodontic devices or appliances. Accordingly, the invention should not be deemed limited to the embodiments set out in detail above, but instead only by a fair scope of the claims that follow along with their equivalents.

We claim:

1. An assembly comprising:
   an orthodontic appliance having a passage;
   an orthodontic device having an opening; and
   an orthodontic coupling pin having an elongated shank and an enlarged head connected to the shank, the shank having an outer end section remote from the head and an intermediate section between the outer end section and the head, wherein the intermediate section extends through the passage, wherein the shank extends through the opening and the opening is located between the passage and the head, wherein the intermediate section is made of a material having a certain yield stress, wherein the outer end section extends past the passage and is remote from the device, and wherein the outer end section is made of a material having a yield stress that is less than the yield stress of the material of the intermediate section.

2. An assembly according to claim 1, wherein the outer end section is made of a material that is annealed to a greater extent than the material of the intermediate section.

3. An assembly according to claim 1, wherein the intermediate section is partially annealed.

4. An assembly according to claim 1, wherein the pin includes a stop fixed to the intermediate section, and wherein the stop is spaced from the head.

5. An assembly according to claim 1, wherein the shank includes an offset section.

6. An assembly according to claim 5, wherein the offset section is located between the intermediate section and the head.

7. An assembly according to claim 1, wherein the intermediate section and the outer end section each have cross-sectional areas in directions transverse to the longitudinal axis of the shank that are approximately equal.

8. An assembly according to claim 1, wherein the head has a somewhat ball-shaped configuration.

9. An assembly according to claim 1, wherein the head has a somewhat "L"-shaped configuration.

10. An assembly according to claim 1, wherein the head has a somewhat "T"-shaped configuration.

11. An assembly according to claim 1, wherein the device is a device for repositioning one jaw relative to the other jaw.

12. An assembly according to claim 1, and including a third section located between the intermediate section and the head.

13. An assembly according to claim 12, wherein the third section has a stiffness that is less than the stiffness of the intermediate section.

14. An orthodontic coupling pin for use with an orthodontic appliance such as a bracket, a buccal tube or the like, the pin having an elongated shank and an enlarged head connected to the shank, the shank having an outer end section remote from the head and an intermediate section between the outer end section and the head, wherein the intermediate section is made of a material having a certain yield stress, wherein the outer end section is made of a material having a yield stress that is less than the yield stress of the material of the intermediate section, and wherein the intermediate section is comprised of a number of wire strands.

15. An assembly according to claim 14, wherein the wire strands of the intermediate section are braided.

16. An orthodontic coupling pin for use with an orthodontic appliance such as a bracket, a buccal tube or the like, the pin having an elongated shank and an enlarged head connected to the shank, the shank having an outer end section remote from the head and an intermediate section between the outer end section and the head, wherein the intermediate section is made of a material having a certain yield stress, wherein the outer end section is made of a material having a yield stress that is less than the yield stress of the material of the intermediate section, and wherein the shank includes a third section located between the intermediate section and the head, wherein the third section has a stiffness that is less than the stiffness of the intermediate section, and wherein the third section is comprised of a number of wire strands.

* * * * *